US00PP09234P

United States Patent [19]

Wyckoff

[11] Patent Number: Plant 9,234

[45] Date of Patent: Aug. 8, 1995

[54] HYBRID TEA ROSE PLANT NAMED 'HAWAIIAN QUEEN MARTHA'

[76] Inventor: Gilbert R. Wyckoff, HCR 2 Box 6026, Keaau, Hi. 96749

[21] Appl. No.: 280,202

[22] Filed: Jul. 25, 1994

[51] Int. Cl.[6] ..... A01H 5/00

[52] U.S. Cl. ..... Plt./11

[58] Field of Search ..... Plt. 11, 12, 17, 18, Plt. 19, 20

*Primary Examiner*—Howard J. Locker

[57] ABSTRACT

A hybrid tea class rose plant with many fine attributes for the home gardener and the exhibitionist: unusual salmon-pink petal coloration, long lasting on bush or as a cut flower; 24 to 30 inch cutting stems and a pleasant, moderately strong fragrance.

3 Drawing Sheets

This present invention relates to a new and distinct variety of rose plant of the hybrid tea class which was originated by me by crossing the variety Kordes Perfecta (U.S. Plant Pat. No. 1,604) (seed parent) with the variety Dothan (pollen parent).

The primary objective of this breeding was to produce a new rose variety which had an unusual and distinctive color combination, along with good foliage and long stems. As both parent roses had much color variation in their breeding, I felt that the cross could produce favorable results. My objective was substantially achieved as evidenced by the following combination of characteristics which distinguish it from its parents as well as from all other varieties of which I am aware, and make it an excellent garden and exhibition type rose:

1. Long cutting stems, 24 to 30 inches.
2. Unusual salmon-pink petal coloration.
3. Moderately strong fragrance.
4. 55 to 60 petals with much substance; long lasting on bush or as a cut flower.

Asexual reproduction by budding, performed in the Hilo, Hi., area, shows that all characteristics and distinctions come true to form and are transmitted through succeeding propagations.

The accompanying photographic illustrations show typical specimens of the vegetative growth and flowers of this new variety in different stages of development, depicted in color as nearly true as it is reasonably possible to attain in color illustrations of this character.

FIG. 1 shows the flower buds in varying stages of opening, foliage and flowering stems.

FIG. 2 further illustrates the bloom, stem, and foliage.

Figure 1:
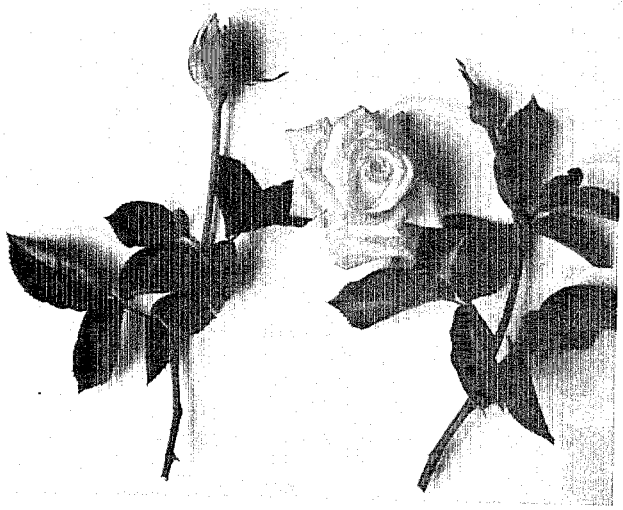
Figure 2:
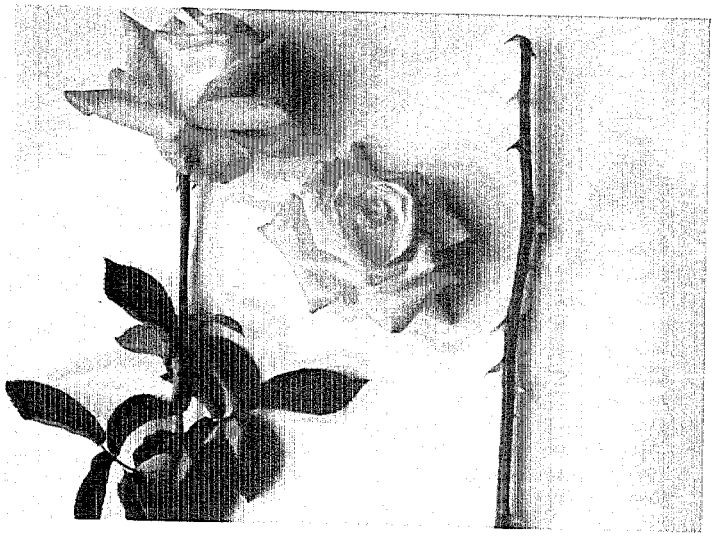
Figure 3:
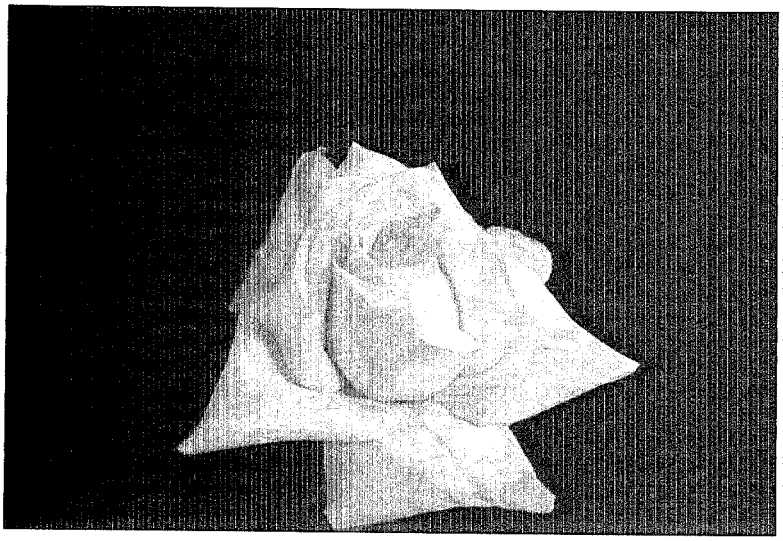
FIG. 3 shows a flower about 25–33% open.
Figure 4:
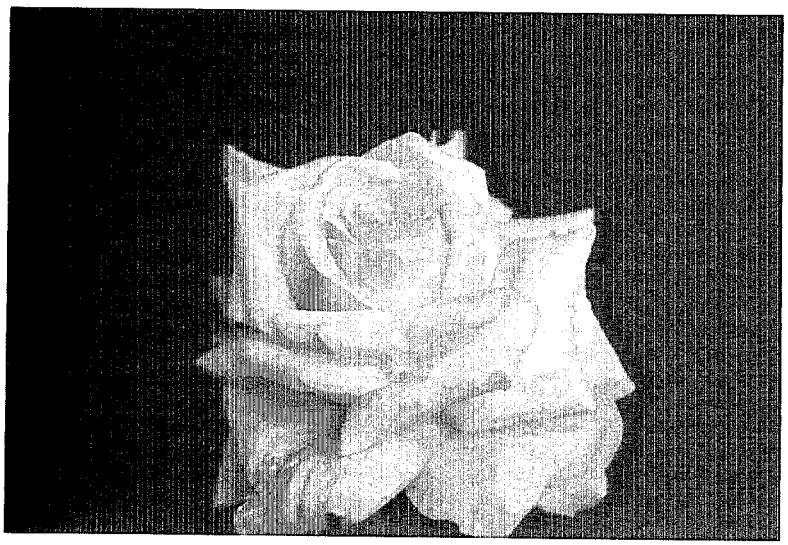
FIG. 4 shows a flower about 80–85% open.
Figure 5:
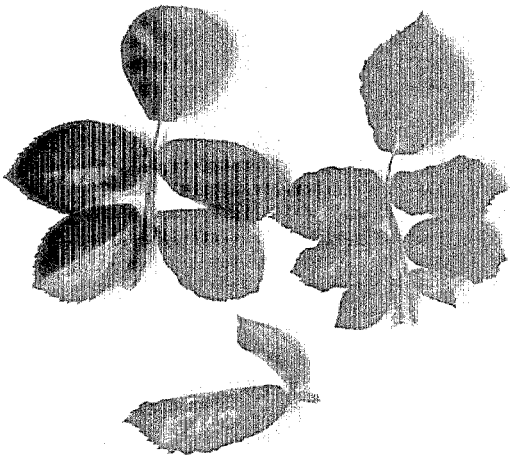

FIG. 5 further illustrates foliage.

The following is a detailed description of my new rose cultivar with color terminology in accordance with the Royal Horticultural Society (London) Colour Chart, except where ordinary dictionary significance of color is indicated.

Parentage:

*Seed parent.*—Kordes Perfecta (U.S. Plant Pat. No. 1,604).

*Pollen parent.*—Dothan.

Classification:

*Botanical.*—*Rosa Hybrida.*

*Commercial.*—Hybrid Tea.

FLOWER

Observations made from specimens grown in outdoor environment in areas surrounding Hilo, Hi., in 1994.

Blooming habit: Recurrent, around 38 to 43 days.

Bud:

*Size.*—About $1\frac{3}{4}$ to 2 inches long when petals begin to unfurl.

*Form.*—Long, pointed, ovoid.

*Color.*—When sepals first divide, the bud color is a combination or mixture of Red Group 36D and Red Group 49D. When half blown, the lower (reverse) sides remain the same, but the upper sides become a combination of the above plus variations of darker shades between Red Group 39A and 39B.

*Sepals.*—Color: Green Group 138B. Surface texture: Smooth.

*Receptacle.*—Color: Green group 140C. Shape: Funnel. Size: Medium to large. Surface: Smooth.

*Peduncle.*—Length: $4\frac{1}{2}$ to 5 inches. Surface: Smooth. Color: Brownish green. Strength: Stiff, erect.

Bloom:

*Size.*—Large. Average open diameter is 5 to $5\frac{1}{2}$ inches.

*Borne.*—Singly.

*Stems.*—Long, average 24 inches up to 30 inches.

*Form.*—High center; retains form to the end; outer petals curl back.

*Petalage.*—Number of petals under normal conditions: 55 to 60.

*Color.*—The upper sides of the petals are an admixture of color combinations, primarily variations between Red Group 36D and Red Group 49D for the lighter shades. For the darker shades, they are variations between Red Group 39A and 39B. The reverse sides are a combination/variation of Red Group 36D and Red Group 49D.

*Variegations: Occasional white or light green streak on guard petals.*

*Discoloration: No general tonality change at end of the first, third, and fifth day.*

*Fragrance: Moderately strong.*

Petals:

*Texture.*—Thick.
*Shape.*—Round, slightly deltoid.
*Form.*—Partly recurved.
*Arrangement.*—Imbricated.
*Persistence.*—Petals drop after 7 days on plant.
*Lastingness.*—On plant, 7 days. As a cut flower, about 10 days.

Reproductive parts:
*Anthers.*—Size: Large. Quantity: Many. Color: Orange. Arrangement: Regular around styles.
*Filaments.*—Color: Orange-red.
*Pollen.*—Color: Orange.
*Styles.*—Color: Red.
*Stigmas.*—Color: Red pink.

Plant form: Bush.

Plant growth: Very vigorous, upright.

Foliage: Number of leaflets on normal, mid-stem leaves: 5 to 7.
*Size.*—Large, mature leaf is 5 to 5½ inches long.
*Quantity.*—Abundant.
*Color.*—New foliage is reddish bronze, both surfaces. Remains like that for 2 weeks or so. Old foliage is semi-gloosy, medium green.

Leaflets:
*Shape.*—Pointed oval.
*Texture.*—Upper side: Leathery, semi-glossy.
*Edge.*—Serrated.

*Serration.*—Medium.
*Petiole rachis.*—Color: green.
*Petiole underside.*—Rough, with prickles.
*Stipules.*—Medium, about ½ inch long, bearded.
*Disease resistance.*—Resistant to black spot and mildew under normal outdoor growing conditions in the East Hawaii area of the Big Island.

Wood:
*New wood.*—Color: Reddish. Bark: Smooth.
*Old wood.*—Color: Green. Bark: Smooth.

Prickles:
*Quantity.*—Ordinary quantity on main canes from base and on laterals from main canes.
*Form.*—Medium, about ⅜ inch long, hooked slightly down.
*Color when young.*—Reddish.

Small prickles:
*Quantity.*—None on main stalks or on laterals.

I claim:

1. A new and distinct variety of rose plant of the hybrid tea class, substantially as herein shown and described, characterized particularly as to novelty by the unique coloration of its blooms and also the long durability of the blooms; and combined with these qualities, the long cutting stems and attractive foliage plus quite good fragrance.

* * * * *